United States Patent [19]
Wheeler

[11] Patent Number: 5,941,248
[45] Date of Patent: Aug. 24, 1999

[54] MONITORING OF PATIENT BEDDING ZONES

[76] Inventor: Alton D. Wheeler, 3940 Fox Meadow La., Pasadena, Tex. 77504

[21] Appl. No.: 08/915,499

[22] Filed: Aug. 20, 1997

[51] Int. Cl.$^6$ ................................................. A61F 5/48
[52] U.S. Cl. ................... 128/885; 128/886; 128/DIG. 25
[58] Field of Search ............................ 128/885, 886, 128/DIG. 25; 73/23.34, 31.06; 340/539, 573, 604, 620

[56] References Cited

U.S. PATENT DOCUMENTS

| | | | |
|---|---|---|---|
| 2,866,454 | 12/1958 | McKenzie | 128/886 |
| 4,163,449 | 8/1979 | Regal | 128/886 |
| 5,137,033 | 8/1992 | Norton | 128/886 |
| 5,291,181 | 3/1994 | DePonte | 128/886 |
| 5,709,222 | 1/1998 | Davallou | 128/885 |

*Primary Examiner*—Michael A. Brown
*Attorney, Agent, or Firm*—William W. Haefliger

[57] ABSTRACT

A method of monitoring patient bedding zone means, which include providing monitoring means spaced from the bedding zone means; providing ducting communicating between the bedding zone means and the monitoring means; effecting air flow via the ducting from the bedding zone means to the monitoring means, and operating the monitoring means to detect waste gaseous contents in the air flow.

23 Claims, 5 Drawing Sheets

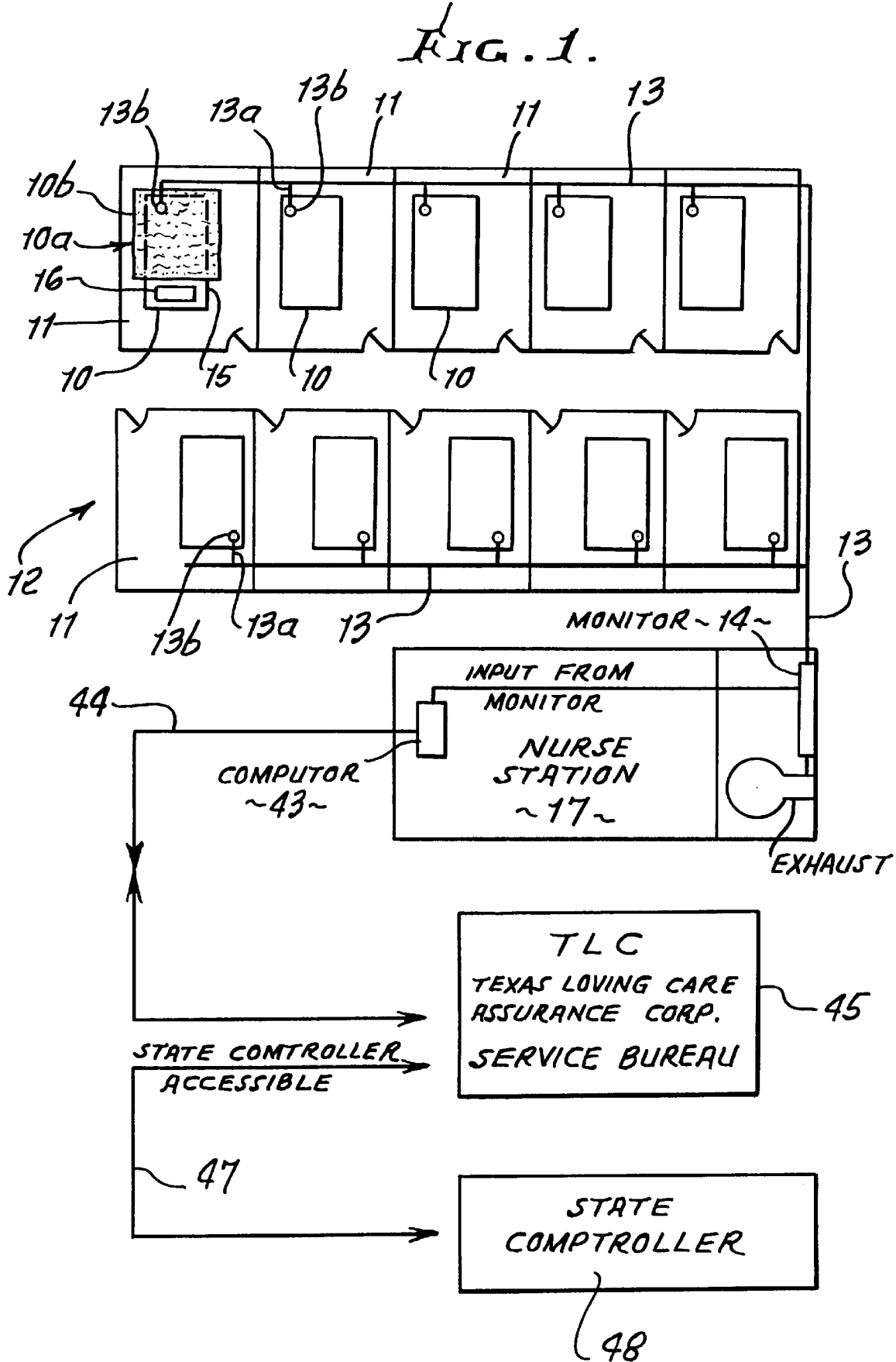

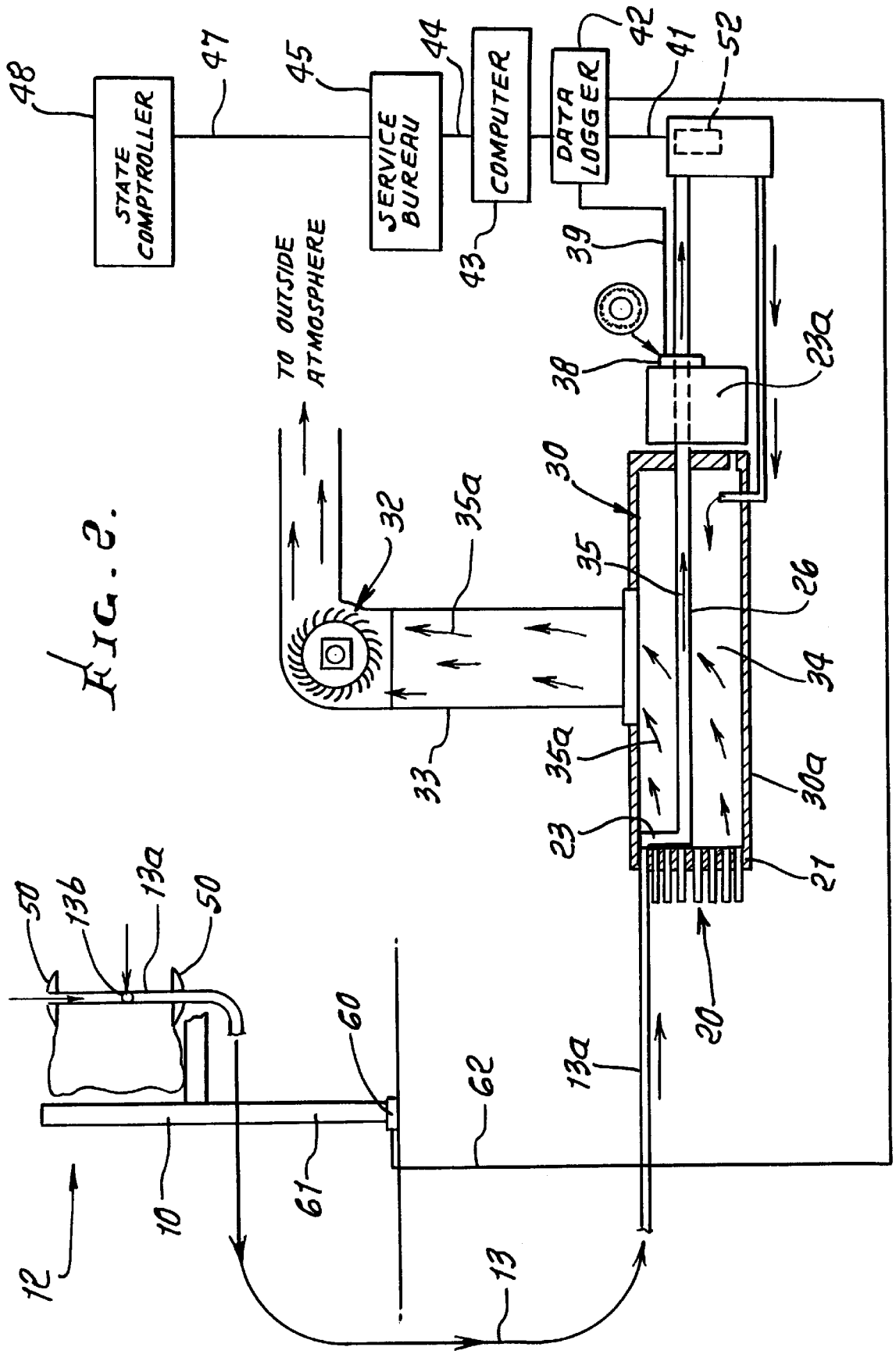

(SAMPLE) HOURLY PATIENT RECORD

HAPPY HARBOUR     ATTENDANT-- SALLY SMITH

NAME MRS. RUTH SMITH      bed #62
ADDRESS MAIN ST. HEART OF TEXAS

| DATE | TIME | AIR QUALITY | | MOVEMENT | | WEIGHT | TEMP |
|---|---|---|---|---|---|---|---|
|  |  | GOOD | POOR | YES | NO |  |  |
| 1\15\97 | 1400 |  | ● |  | ● | 92 LBS. | NORMAL |
| WARNING ISSUED | | | IF THIS CONDITION IS NOT CORRECTED WITHIN THE NEXT HOUR A PENALTY OF $___ WILL BE INVOKED. | | | | |

FIG. 4.

MONITORING OF PATIENT BEDDING ZONES

BACKGROUND OF THE INVENTION

This invention relates generally to monitoring of bedridden people, as for example nursing home patients, and more particularly to monitory of incontinent conditions of such people or patients.

There is constant and great need for improved methods for handling incontinent, bedridden people from both physical health and morale standpoints. It is very undesirable, yet quite common, to delay for substantial time periods attendance to such incontinent conditions. For example, in a large nursing home, with many bedridden patients, many of whom are very weak and unable to summon attention, there may be substantial numbers of such patients who need attention, but for whom attention will be delayed, because the nursing staff may not know of need, or be delayed in checking need, for attention.

SUMMARY OF THE INVENTION

It is a major object of the invention to provide improved method and means meeting the above need, particularly for a large number of patients lying bedridden as in a nursing home. Basically, the method of the invention includes the steps;

a) providing monitoring means spaced from the bedding zone means, b) providing ducting communicating between the bedding zone means and the monitoring means, c) effecting air flow via the ducting from the bedding zone means to the monitoring means, and d) operating the monitoring means to detect waste gaseous contents in such air flow.

As will appear, the bedding zone means may typically include bedding zones of multiple patient beds, as in a nursing home for example, and the effecting of air flow may include selectively flowing air from such zones to the monitoring means. Alternatively, there may be centralized monitors, one for each bedding zone.

Another object includes providing and operating control valve means in series with said ducting to establish air flow from selected individual bedding zones to the monitoring means.

Yet another object includes providing a manifold, providing individual ducts from the bedding zones to the manifold, and applying suction to the manifold, as via operation of a blower, in order to effect air flow in all or many of the ducts toward and into the manifold. Advantage can then be taken of the momentum of air flow in the ducts, to select any one duct for sampling of moving air flow, as in a monitoring means connected to that one duct while air flows therein. An additional blower at the monitor may be used to assure continued air flow to the monitor, via any one selected duct, the ducts being selectable in a sequence, as by operation of a rotary sampling valve. Waste gaseous content of the air flow typically includes methane, and/or ammonia.

It is a further object to provide multiple ducts having inlets which communicate directly with bedding sampling zones beneath bed covers at the multiple patient beds. For this purpose, the multiple ducts may be attached to structure at the bedding zones.

Apparatus incorporating the invention basically comprises:

a) monitoring means spaced form the bedding zone means, b) ducting communicating between the bedding zone means and the monitoring means, c) means for effecting air flow via the ducting to the monitoring means, d) said monitoring means including a detector to detect waste gaseous content of said air flow.

The monitoring means may include detector means to detect methane and ammonia in the air flow, and also recording means to record gaseous content of the flow, for example in terms of determining or discriminating between methane and ammonia, and also the intensity levels of these constituents, as in percentage of the total flow. The monitoring means may include signaling means to alert an attendant at a centralized monitor, as to need for attention to a particular patient. To this end, a rotary scanning valve may be provided to sequentially and repeatedly connect ducts in a group to the monitoring means.

Yet another object is to provide a central valve means, as referred to, located between the ducts and said manifold and rotatable into sequential connection in series with the individual ducts, the remaining ducts directly connected with the manifold means to which suction is applied, for exhausting of air in the manifold, and for establishing air flow in the ducts to the manifold means.

These and other objects and advantages of the invention, as well as the details of an illustrative embodiment, will be more fully understood from the following specification and drawings, in which:

DRAWING DESCRIPTION

FIG. 1 is a system diagram;

FIG. 2 is a schematic view of a monitoring means and associated duct sampling apparatus;

FIG. 4 is a typical monitor output.

DETAILED DESCRIPTION

Figure 2A:
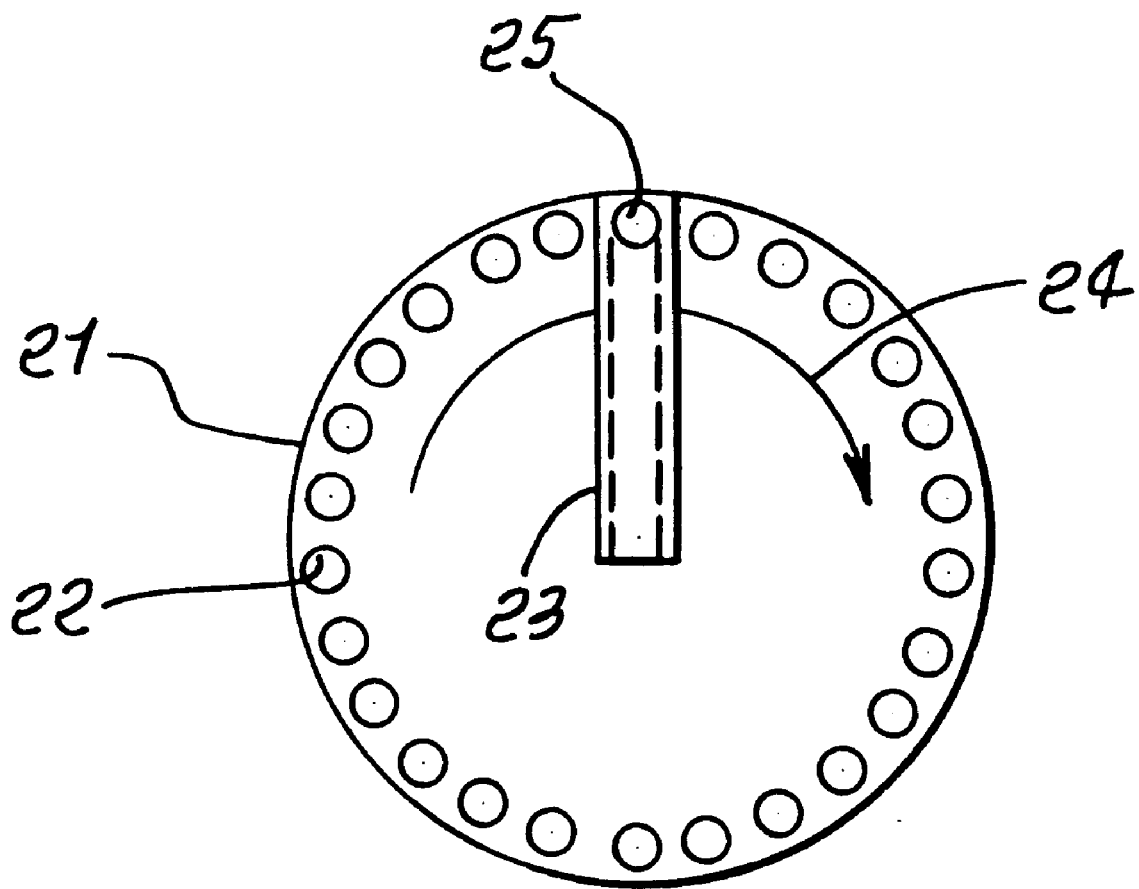
FIG. 2a is an end view of a valve body.

In FIG. 1, multiple patients beds 10 are indicated as in rooms 11 in a nursing home 12. Ducting generally indicated at 13 is extended between beds 10 and a monitoring means 14 spaced from bedding zones 10a at the beds. Such zones may include bed covers 10b, and the ducting may include individual ducts 13a having inlets 13b extended beneath the bed covers, as for example between the covers and a mattress 15. A patient's pillow is shown at 16. The monitoring means 14 is shown as located, for example, at a nursing station 17, whereby a single nurse may observe the monitoring means (as for example a computer screen), in order to quickly note an indicated need, at any of the beds, for attention to an incontinent patient. That need may then quickly be met, as by an orderly or attendant.

Figure 3:
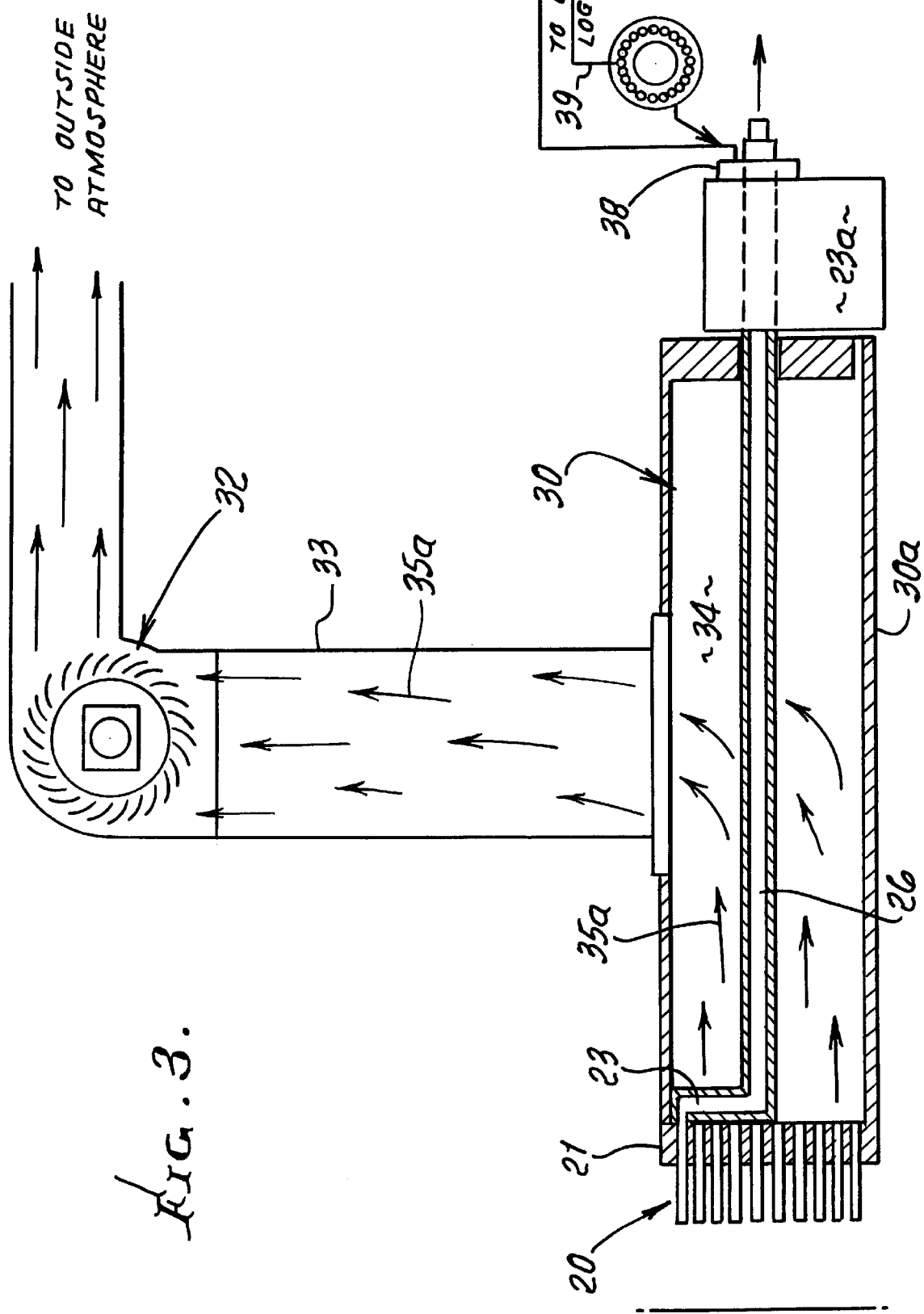
FIG. 3 is an enlarged view of a portion of the FIG. 2 apparatus.

Extending the description to FIGS. 2, 2a and 3, the ducts 13a are shown as terminating at a circular series of tubular connectors 20, one for each duct, i.e. one for each bed. The connectors extend within a valve body 21, to present openings 22 in a common plane, wiped by a valve rotor 23, rotatably driven at 23a. Note arrow 24 indicating direction of rotation of the rotor. The rotor is ported as at 25 to conduct air from any selected duct to a conduit 26 leading to 19 monitor 14.

A common air manifold 30 is enclosed by walls 30a, and openly communicates with all of the connectors 20 via ports 22 in the valve body, except the connector 20 being sampled by the rotor 23. An exhaust blower 32 in discharge duct 33, applies suction to the manifold interior 34, whereby air is drawn via all the ducts 13a toward and into the manifold. Accordingly, air flow is established in each duct so that when it is sampled, the air flow will continue, as indicated by arrows 35, toward and into the monitor. Exhaust air flow is indicated by arrows 35a. Monitored air is restored via line 36 to the manifold interior.

A rotary switch 38, driven by 23a, provides an output at 39 connected to logger 42 which indicates which duct 13a is being sampled, and therefore monitoring of air flow from a selected duct is correlated with the patient's bed zone to which the duct is connected. Output 41 from the monitor, as well as output 39, are connected via data logger 42 with a computer 41 the screen of which is observed by the attendant, to note which patient needs attention. The computer may have an output at 44 connected to a service bureau 45, to which a large number of nursing home monitor outputs are connected, as at 46, for statistical analysis, control of the monitor, and other purposes. A line to a government regulatory unit 48 is indicated at 47, to supply information such as quickness of response of attendants to patients' indicated needs, whereby the quality of nursing home operation may be monitored.

Ducts 13a may be suitably attached as by retention buttons 50, to bedding structure such as mattresses. See FIG. 2.

Waste gas detector means is indicated at 52 in FIG. 2. Such detectors, as for ammonia and methane, are known in the art.

FIG. 4 shows one type of data output on the computer screen. Presence of waste gas is shown in terms of "poor" air quality.

The system of the present invention provides or may provide the following advantages:

Identifies each patient and the attendant on duty.

Records each time the patient is checked.

Verifies when the patient is turned.

Monitors and removes methane and ammonia from under the bed covers.

Indicates when the environment beneath the cover has been corrected.

Signifies instant warnings and invokes penalties.

Provides the data concerning a particular patient to a relative through a 900 information system.

FIG. 2 also shows a bed weight sensor or sensors 60 under a patient bed port 61, and connected at 62 with the data logger to provide data as to total patient and bed weight.

I claim:

1. A method of monitoring patient bedding zone means, which include
    a) providing monitoring means spaced from the bedding zone means,
    b) providing ducting communicating between the bedding zone means and the monitoring means, and
    c) effecting air flow via the ducting from the bedding zone means to the monitoring means, and
    d) operating the monitoring means to detect waste gaseous contents in said air flow.

2. The method of claim 1 wherein said bedding zone means includes bedding zones of multiple patient beds, and said effecting step includes selectively flowing air from different bedding zones to the monitoring means.

3. The method of claim 2 including providing and operating control valve means in series with said ducting to establish air flow from selected individual bedding zones to said monitoring means.

4. The method of claim 2 including providing a manifold, said providing of ducting including providing individual ducts from the multiple bedding zones to said manifold, said effecting of air flow including applying suction to said manifold to effect air flow via said individual ducts to said manifold.

5. The method of claim 4 including providing and operating contral valve means to selectively connect said individual ducts with said monitoring means.

6. The method of claim 2 wherein said bedding zones include individual bed covers, said ducts have inlets, and including communicating said inlets with bed zones beneath said covers of said respective bedding zones; and attaching the ducts to structure associated with bedding zones.

7. The method of claim 1 wherein said waste gaseous content includes methane and ammonia.

8. The method of claim 1 wherein said operating of said monitoring means includes recording the waste gaseous content of said air flow.

9. The method of claim 8 wherein said recording includes providing data corresponding to said waste gaseous content of said air flow.

10. The method of claim 9 including providing said data via a computer to at least one of the following:
    i) a service bureau
    ii) a governmental regulating authority.

11. In apparatus for monitoring patient bedding zone means, the combination comprising
    a) monitoring means spaced form the bedding zone means,
    b) ducting communicating between the bedding zone means and the monitoring means,
    c) means for effecting air flow via the ducting to the monitoring means,
    d) said monitoring means including a detector to detect waste gaseous content of said air flow.

12. The combination of claim 11 wherein said bedding zone means includes bedding zones of multiple patient beds, and said ducting communicates said multiple bedding zones with said monitoring means.

13. The combination of claim 12 including control valve means in series with said ducting to establish air flow from selected individual bedding zones to said monitoring means.

14. The combination of claim 13 wherein said ducts have inlets respectively communicating with bedding zones of multiple patient beds, respectively.

15. The combination of claim 14 wherein said bedding zones include patient bed covers, and said ducts have inlets in communication with the bedding zones beneath said covers, respectively.

16. The combination of claim 12 including a manifold, said ducting including individual ducts communicating individual bedding zones with said manifold, and a blower for applying suction to said manifold to enhance air flow via the individual ducts to the manifold.

17. The combination of claim 16 including control valve means connectable in series with said ducts to selectively connect individual ducts with said monitoring means.

18. The combination of claim 17 wherein said control valve means is located between said ducts and said manifold and is rotatable into sequential communication in series with the individual ducts, the remaining ducts directly connected with the manifold means to which suction is applied, for exhausting of air from bed zones via the manifold, and for establishing air flow in the ducts to the manifold.

19. The combination of claim 17 including a rotary drive to rotatably drive the control valve, a rotary patient identification switch driven by said drive, and circuitry connected to said switch and to said indicator means to enable correlation of patients with the outputs of said monitoring means.

20. The combination of claim 19 including also patient weight sensing means connected to said circuitry.

21. The combination of claim 11 wherein said monitoring means includes detector means to detect methane and ammonia in said air flow.

22. The combination of claim 11 wherein said monitoring means includes means to detect and record the waste gaseous contact of said air flow, in the form of recorded data.

23. The combination of claim 22 including a communication line or lines to transmit said data to one of the following:
  i) a service bureau
  ii) a governmental regulatory authority.

* * * * *